United States Patent [19]
Wegner et al.

[11] Patent Number: 5,089,662
[45] Date of Patent: Feb. 18, 1992

[54] 2,2-DIFLUOROCYCLOPROPYLETHANE DERIVATIVES, PROCESSES FOR THEIR PREPARATION AND THEIR USE AS PESTICIDES

[75] Inventors: Peter Wegner; Hartmut Joppien; Günter Hömberger; Arnim Köhn, all of Berlin, Fed. Rep. of Germany

[73] Assignee: Schering Aktiengesellschaft, Fed. Rep. of Germany

[21] Appl. No.: 621,618

[22] Filed: Dec. 3, 1990

Related U.S. Application Data

[62] Division of Ser. No. 276,870, Nov. 28, 1988, Pat. No. 4,983,630.

Foreign Application Priority Data

Nov. 27, 1987 [DE] Fed. Rep. of Germany ....... 3740840

[51] Int. Cl.$^5$ ................. C07C 61/; C07C 04
[52] U.S. Cl. .................. 562/506; 562/867
[58] Field of Search ............... 562/867, 506

[56] References Cited

U.S. PATENT DOCUMENTS

| | | | |
|---|---|---|---|
| 3,509,197 | 4/1970 | Mitsch | 560/124 |
| 3,759,964 | 9/1973 | Siddall | 560/124 |
| 3,927,068 | 12/1975 | Searle | 560/124 |
| 4,983,630 | 1/1991 | Wegner | 514/531 |

FOREIGN PATENT DOCUMENTS

| | | | |
|---|---|---|---|
| 2077 | 5/1979 | European Pat. Off. | 560/124 |
| 2892 | 10/1981 | World Int. Prop. O. | 560/124 |

OTHER PUBLICATIONS

Okada, Agric. Biol. Chem., 44 (11) pp. 2595-2599 (1980).
Kobayashi, Tetrahedron Letters, 22, pp. 5297-5300 (1981).
Taguchi, Nippon Kaguku Kaishi, No. 11, pp. 2177-2184 (1985).

*Primary Examiner*—Michael L. Shippen
*Attorney, Agent, or Firm*—Ostrolenk, Faber, Gerb & Soffen

[57] ABSTRACT

There are provided new 2,2-difluorocyclopropylethane derivatives of general formula I

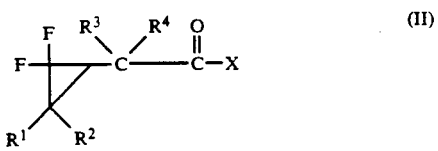

in which A, B and $R^{1-5}$ have the meanings given in the description and processes for their preparation. The compounds of the invention can be used as pesticides, especially against insects and mites.

5 Claims, No Drawings

2,2-DIFLUOROCYCLOPROPYLETHANE DERIVATIVES, PROCESSES FOR THEIR PREPARATION AND THEIR USE AS PESTICIDES

This is a division of application Ser. No. 07/276,870 filed Nov. 28, 1988, now U.S. Pat. No. 4,983,630.

The invention relates to new 2,2-difluorocyclopropylethane derivatives their preparation and intermediates for their preparation as well as their use as pesticides especially against insects and mites.

It is already known that cyclopropane compounds possess acaricidal properties (U.S. Pat. No. 3,995,054).

The disadvantage of the known compounds however is that the insecticidal and acaricidal activity is not sufficiently high.

The object of the present invention is to provide new compounds that combat insects and mites better than compounds known for this purpose.

It has now been found that 2,2-difluorocyclopropylethane derivatives of general formula I

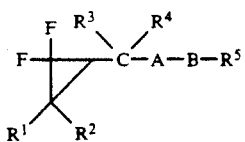

in which $R^{1-4}$ are the same or different and are hydrogen, $C_{1-6}$-alkyl or halogen, $R^5$ is hydrogen,
  an alkali metal or a corresponding equivalent of a divalent metal,
  $C_{1-20}$-alkyl, $C_{2-20}$-alkenyl, $C_{2-20}$-alkynyl,
  halo-$C_{1-10}$-alkyl,
  $C_{3-6}$-cycloalkyl,
  $C_{1-3}$-alkyl-$C_{3-6}$-cycloalkyl,
  $C_{3-6}$-cycloalkyl-$C_{1-6}$-alkyl,
  halo-$C_{3-6}$-cycloalkyl-$C_{1-6}$-alkyl,
  decahydronaphthalinyl,
  indanyl,
  adamantyl,
  adamantylmethyl,
  difluorocyclopropylethylcarbonyloxy-$C_{1-10}$-alkyl,
  difluorocyclopropylcarbonyloxydecahydronaphthalinyl,
  difluorocyclopropylcarbonyloxy-$C_{1-3}$-alkoxy-$C_{1-3}$-alkyl,
  phenyl-$C_{1-6}$-alkyl,
  phenyl-$C_{2-6}$-alkenyl,
  halobenzyl,
  $C_{1-4}$-alkylbenzyl,
  $C_{1-3}$-alkoxyphenyl-$C_{1-6}$-alkyl,
  phenoxybenzyl,
  α-cyanophenoxybenzyl,
  α-$C_{1-3}$-alkylphenoxybenzyl,
  ethoxy-(α-trifluoromethyl)benzyl,
  halophenyl(cyclopropyl)-$C_{1-3}$-alkyl,
  halophenoxy-$C_{1-6}$-alkyl,
  naphthyl-$C_{1-6}$-alkyl,
  methylthiazolyl-$C_{1-6}$-alkyl,
  tris(difluorocyclopropylmethylcarbonyloxymethyl)methyl,
  tri($C_{4-8}$-cycloalkyl)stannyl,
  aryl, optionally substituted by one or more of $C_{1-20}$-alkyl, halo-$C_{1-6}$-alkyl, $C_{1-16}$-alkoxy, halo-$C_{1-6}$-alkoxy, phenyl-$C_{1-6}$-alkyl, phenyl-$C_{1-6}$-alkoxy, $C_{3-10}$-cycloalkoxy, halo-$C_{3-10}$-cycloalkoxy, $C_{3-6}$-cycloalkylalkoxy, halo-$C_{3-6}$-cycloalkylalkoxy, $C_{2-6}$-alkenyloxy, halo-$C_{2-6}$-alkenyloxy, $C_{2-6}$-alkynyloxy, halo-$C_{2-6}$-alkynyloxy, alkylsulphonyloxy, alkylphenylsulphonyloxy, haloalkylsulphonyloxy, phenyl, halogen, amino, cyano, hydroxy, nitro, aryloxy, heteroaryloxy, haloaryloxy, arylamino, haloarylamino, $C_{1-6}$-alkoxycarbonyl, $C_{1-6}$-alkoxycarbonylmethyl, halo-$C_{1-6}$-alkoxycarbonyl, $C_{1-2}$-alkyldioxy, $C_{1-6}$-alkylthio, halo-$C_{3-6}$-cycloalkylalkylamino, halo-$C_{3-6}$-cycloalkylalkyl carbonyloxy, $C_{1-6}$-alkylamino or di-$C_{1-6}$-alkylamino, heteroaryl, optionally substituted by halogen, $C_{1-3}$-alkyl or halo-$C_{1-3}$-alkyl, or the group $CONHR^8$, in which $R^8$ is hydrogen, $C_{1-6}$-alkyl or phenyl, optionally substituted by one or more of $C_{1-6}$-alkyl, halo-$C_{1-6}$-alkyl, $C_{1-16}$-alkoxy, halo-$C_{1-6}$-alkoxy, phenyl-$C_{1-6}$-alkoxy, $C_{3-10}$-cycloalkoxy, halo-$C_{3-10}$-cycloalkoxy, $C_{3-6}$-cycloalkylalkoxy, halo-$C_{3-6}$-cycloalkylalkoxy, $C_{2-6}$-alkenyloxy, halo-$C_{2-6}$-alkenyloxy, $C_{2-6}$-alkynyloxy, halo-$C_{2-6}$-alkynyloxy, alkylsulphonyloxy, haloalkylsulphonyloxy, phenyl, halogen, amino, cyano, hydroxy, nitro, aryloxy, haloaryloxy, arylamino, haloarylamino, $C_{1-6}$-alkoxycarbonyl, halo-$C_{1-6}$-alkoxycarbonyl, $C_{1-2}$-alkyldioxy, $C_{1-6}$-alkylthio, halo-$C_{3-6}$-cycloalkylalkylamino, $C_{1-6}$-alkylamino or di-$C_{1-6}$-alkylamino, A is carbonyl, thiocarbonyl or methylene, B is oxygen, sulphur or $NR^6$, in which, $R^6$ is hydrogen, $C_{1-6}$-alkyl or $C_{3-12}$-cycloalkyl, phenyl or $COR^7$, in which $R^7$ is $C_{1-6}$-alkyl; halo-$C_{1-6}$-alkyl; phenyl, optionally substituted by one or more of $C_{1-6}$-alkyl, halo-$C_{1-6}$-alkyl, $C_{1-16}$-alkoxy, halo-$C_{1-6}$-alkoxy, phenyl-$C_{1-6}$-alkoxy, $C_{3-10}$-cycloalkoxy, halo-$C_{3-10}$-cycloalkoxy, $C_{3-6}$-cycloalkylalkoxy, halo-$C_{3-6}$-cycloalkylalkoxy, $C_{2-6}$-alkenyloxy, halo-$C_{2-6}$-alkenyloxy, $C_{2-6}$-alkynyloxy, halo-$C_{2-6}$-alkynyloxy, alkylsulphonyloxy, haloalkylsulphonyloxy, phenyl, halogen, amino, cyano, hydroxy, nitro, aryloxy, haloaryloxy, arylamino, haloarylamino, $C_{1-6}$-alkoxycarbonyl, halo-$C_{1-6}$-alkoxycarbonyl, $C_{1-2}$-alkyldioxy, $C_{1-6}$-alkylthio, halo-$C_{3-6}$-cycloalkylalkylamino, $C_{1-6}$-alkylamino or di-$C_{1-6}$-alkylamino; $C_{3-6}$-cycloalkyl; $C_{1-6}$-alkylamino or $C_{1-6}$-alkoxy, show a better insecticidal and acaricidal activity in comparison with known compounds.

The term alkyl includes straight and branched chain groups.

The term alkenyl includes straight and branched chain groups that can contain one or more double bonds.

The term alkynyl includes straight and branched chain groups that can contain one or more triple bonds.

The term aryl stands for one to three ringed aromatic groups, such as e.g. phenyl, naphthyl or phenanthryl.

The term heteroaryl stands for a 5- or 6-membered ring that contains one or more nitrogen, oxygen or sulphur atoms that can be saturated, partially saturated or unsaturated and can optionally carry a fused benzo ring, such as e.g. pyridine, thiazole or chromene.

$R^5$ and $R^6$ can optionally together with the nitrogen to which they are attached form a saturated or unsaturated ring, such as morpholino, piperidino, pyrrolo, imidazolo or triazolo.

The compounds of formula I are present as racemic mixtures of the optically active isomers. The invention consequently is not limited just to the isomeric mixture but also includes each individual isomer of the compounds of the invention.

2,2-Difluorocyclopropylethane derivatives of general formula I which show particularly good activity are those where:
A is carbonyl,
B is oxygen or NH,
$R^{1-4}$ are hydrogen and
$R^5$ is hydrogen or $C_{1-20}$-alkyl, $C_{1-20}$-alkenyl, $C_{1-20}$-alkynyl, m-phenoxybenzyl or naphthylmethyl.

The invention also relates to compounds of formula II

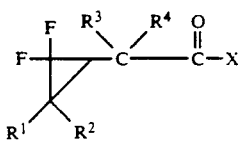

as intermediates in the production of compounds of formula I in which
$R^{1-4}$ have the meanings given in formula I and
X is OH, Cl or Br.

The new intermediates are particularly suitable for preparing compounds of formula I in which A is carbonyl.

The 2,2-difluorocyclopropylethane derivatives of the invention of formula I, in which A is carbonyl, can be prepared,
A) by reacting an acid halide of general formula II

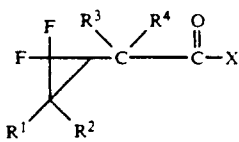

in which
$R^{1-4}$ have the meanings given in formula I and
X is chloro or bromo,
with an alcohol or amine of general formula III

in which B and $R^5$ have the meanings given in formula I, optionally in a solvent and in the presence of an acid acceptor, or
B) by reacting a free acid of general formula IV

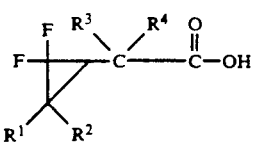

in which
$R^{1-4}$ have the meanings given in formula I, with an alcohol or amine of formula III, optionally using a solvent in the presence of a catalyst, or
C) by reacting an acid of general formula V,

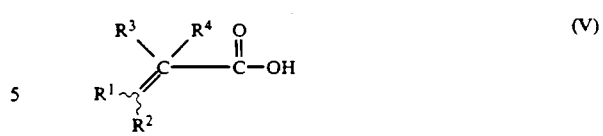

in which $R^{1-4}$ have the meanings given in formula I, with an alcohol or amine of formula III, optionally, in a solvent in the presence of a catalyst or a dehydrating agent, to give an intermediate of formula VI

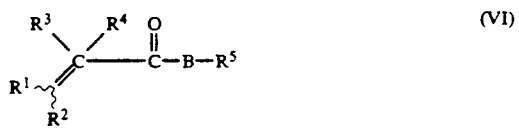

in which B and $R^{1-5}$ have the meanings given in formula I, and reacting this with difluorocarbene, in the presence of an inert solvent, or
when A is methylene and
B is $NR^6$, the compounds can be prepared,
D) by reacting an amide of the specific formula I

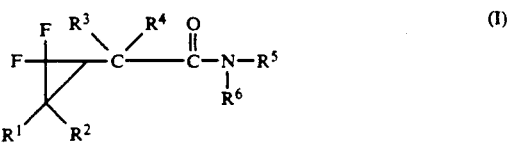

in which
$R^{1-6}$ have the meanings given in formula I, with a reducing agent, optionally in a solvent and in the presence of a catalyst, or
E) by reacting an amine of general formula VII

in which
$R^5$ and $R^6$ have the meanings given in formula I, in the presence of a base, with a halide of general formula VIII

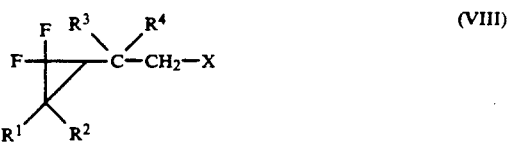

in which
$R^{1-4}$ have the meanings given in formula I and X is chlorine or bromine, optionally using a solvent, or
F) by reacting compounds of general formula IX,

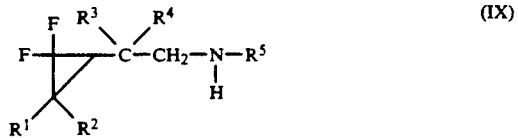

in which $R^{1-5}$ have the meanings given in formula I, and prepared according to reaction variants D) or E), with acid halides of general formula X $$X-\overset{O}{\underset{\|}{C}}-R^8 \qquad (X)$$

in which $R^8$ has the meaning given in formula I and X is chlorine or bromine, optionally using a solvent in the presence of an acid acceptor, or when B is oxygen, the compounds can be prepared,
G) by reacting an alcohol of general formula XI

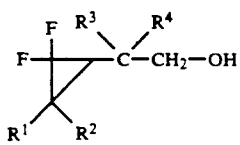

(XI)

in which
$R^{1-4}$ have the meanings given in formula I, with an isocyanate of general formula XII $$O=C=N-R^8 \qquad (XII)$$

in which $R^8$ has the meaning given in formula I, optionally using a solvent in the presence of a catalyst and optionally, subsequently separating the racemic mixture into optically active isomers according to known methods.

Conventional basic materials are suitable as acid acceptors for reaction variants A) and F), especially aliphatic, aromatic and heterocyclic amines, such as e.g. triethylamine, dimethylamine, piperidine, dimethylaniline, dimethylbenzylamine, pyridine and dimethylaminopyridine or inorganic bases such as oxides, hydroxides, carbonates, hydrogen carbonates and alcoholates of alkali- and alkaline earth metals, such as potassium hydroxide, sodium hydroxide, sodium and potassium carbonate.

Suitable solvents are the previously named acid acceptors themselves or inert solvents or mixtures of these.

Examples include aliphatic, alicyclic and aromatic hydrocarbons which can optionally be chlorinated, such as hexane, cyclohexane, petroleum ether, benzene, toluene, xylene, dichloromethane, chloroform, carbon tetrachloride, 1,2-dichloroethane, trichloroethylene and chlorobenzene; ethers, such as diethyl ether, methyl ethyl ether, diisopropyl ether, dibutyl ether, dioxane and tetrahydrofuran; ketones, such as acetone, methyl ethyl ketone, methyl isopropyl ketone and methyl isobutyl ketone; nitriles, such as acetonitrile, propionitrile and benzonitrile; esters, such as ethyl acetate and amyl acetate; amides, such as dimethylformamide and dimethylacetamide; as well as sulphones and sulphoxides, such as dimethyl sulphoxide and sulpholane.

The reaction can be carried out within a wide temperature range. In general it is carried out at a temperature between $-20°$ C. and the boiling point of the reaction mixture, preferably between 20° and 200° C.

The reaction can be carried out at normal pressure, or even at higher or reduced pressure.

Catalysts which are suitable for carrying out reaction variant B include strong acids, such as sulphuric acid, hydrogen halides, sulphonic acids and acidic ion exchange reagents. It is advantageous if water or the ester of formula I is removed from the reaction mixture, for example by azeotropic distillation or by binding the water to sulphuric acid or a hydrogen halide acid.

Reaction variant B can be carried out under similar reaction conditions as far as temperature and pressure are concerned, and in the same solvents or mixtures thereof, as for reaction variant A.

For the preparation of the intermediate compound VI, used in reaction variant C, the same acid catalysts and inert solvents named for reaction variant B can be used. Especially suitable for the esterification is to bind the water by a combination of triphenylphosphine and an axodicarboxylate ester. (Synthesis 1981, 1). Also suitable are classical dehydrating agents, such as concentrated sulphuric acid, anhydrous salts of inorganic acids, such as magnesium sulphate or calcium chloride, carbodiimides, such as dicyclohexylcarbodiimide and also zeolites. The carbene reaction is however preferably carried out in an ether, such as diglyme, triglyme or tetraglyme. The production of difluorocarbene can be carried out according to well known methods in the technical literature (Burton and Hahnfeld, Fluorine Chem. Rev. 8 (1977), 119 ff).

Suitable substances for generating difluorcarbene are for example alkali metal chlorodifluoroacetates, such as sodium chlorodifluoroacetate; halodifluorohydrocarbons, such as chlorodifluoromethane; organo tin compounds, such as trimethyl(trifluoromethyl)tin; organo mercury compounds, such as phenyl(trifluoromethyl)mercury; and organo phosphorus compounds such as tris(trifluoromethyl)difluorophosphorane and triphenyl(bromodifluoromethyl)phosphonium bromide.

Reaction variant D can be carried out under similar reaction conditions as far as temperature and pressure are concerned, and in the same solvents or mixtures thereof, as for reaction variant A.

Sutable reagents for carrying out reaction variant D are e.g. lithium aluminium hydride, borane or sodium borohydride in the presence of cobalt dichloride, acetic acid or trifluoroacetic acid.

Reaction variant E can be carried out under similar reaction conditions as far as temperature and pressure are concerned, and in the same solvents or mixtures thereof, as for reaction variant A.

Sutable bases for carrying out reaction variant E are e.g. potassium carbonate, potassium hydroxide, sodium hydroxide or potassium tert-butylate.

Reaction variant G can be carried out under similar reaction conditions as far as temperature and pressure are concerned, and in the same solvents or mixtures thereof, as for reaction variant A.

The preparation of the optical isomers of the invention can be carried out in conventional manner, for example by treatment of compounds of formula II with a chiral reagent, such as e.g. an optically active amine or an optically active alcohol and separation of the diastereomers so obtained by physical methods (Tetrahedron 33, 2725 (1977)), such as e.g., recrystallisation, distillation or flash chromatography. By a subsequent hydrolytic cleaving, that can be acid or base catalysed, the optical isomers of the free acids of general formula IV are obtained, which can be converted by procees variant B to the compounds of the invention.

Further, the mixtures of optical isomers of general formula I, obtained from the synthesis can be separated into the enantiomers by chromatography on chiral stationary phases, such as e.g. cyclodextrins, starch or optically active amino acids bound to polymers (Angew. Chem. 92, 14 (1980)).

The compounds of the invention prepared by the above described processes can be isolated from the reaction mixture in conventional manner, for example by distillation of the solvent used, at normal or reduced pressure, by precipitation with water or by extraction.

A higher degree of purity can be achieved as general rule by thin layer chromatography purification, by fractional distillation or recrystallisation.

The compounds of the invention are, as a rule, almost colourless and odourless viscous oils or crystals that are almost insoluble in water, have limited solubility in aliphatic hydrocarbons, such as petroleum ether, hexane, pentane and cyclohexane, and highly soluble in chlorinated hydrocarbons, such as chloroform, methylene dichloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The acid halide of formula X, the acid of formula V, the alcohol and amine of formulae III and VII, as well as the isocyanate of formula XII, are known or can be prepared by known methods.

The acid halide of formula II, the halide of formula VIII, as well as the alcohol of formula XI, can be prepared by known methods.

The compounds of the invention are distinguished by good insecticidal activity and especially good acaricidal activity and thus represent a valuable improvement in the state of the art. Based on their activity against a wide range of sucking arthropods, the compounds of the invention can be used not only against pests in crops but also for combating human and domestic animal parasites. The activity of the compounds of the invention is of particular importance against paarasites which have developed resistance to other substances. Since the compounds of the invention are taken up by the plants and transported systemically, they can also be applied to the soil and thus reach those plant parts that cannot be treated directly.

Examples of insects and mites, including animal ectoparasites, that can be combated by the compounds of the invention include Lepidoptera, such as *Plutella xylostella, Spodoptera littoralis, Heliothis armigera* and *Pieris brassicae*; Diptera, such as *Musca domestica, Ceratitis capitata, Erioischia brassicae, Lucilia sericata* and *Aedes aegypti*; Homoptera, including aphids such as *Megoura viciae* and *Nilaparvata lugens*; Coleoptera, such as *Phaedon cochleariae, Anthonomus grandis, Epilachna varivestis* and corn rootworms (Diabrotica spp. e.g. *Diabrotica undecimpunctata*); Orthoptera, such as *Blattella germanica*; ticks, such as *Boophilus microplus* and lice, such as *Damalinia bovis* and *Linognathus vituli*, as well as spider mites such as *Tetranychus urticae* and *Panonychus ulmi*.

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may also include phospholipids, e.g. such as from the group phosphatidylcholine, hydrogenated phosphatidylcholine, phosphatidylethanolamine, N-acyl-phosphatidylethanolamine, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

Formulations can be prepared, for example, from the following ingredients.

A. WETTABLE POWDER 20 percent by weight active ingredient
35 percent by weight bentonite
8 percent by weight calcium lignosulphonate
2 percent by weight of the sodium salt of N-methyl-N-oleyltaurine
35 percent by weight silicic acid.

B. PASTE 45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water.

C. EMULSIFIABLE CONCENTRATE 20 percent by weight active ingredient
75 percent by weight isophorone
5 percent by weight of a mixture based on the sodium salt of N-methyl-N-oleyltaurine and calcium lignosulphonate.

The following Examples illustrate the preparation of compounds of the invention.

EXAMPLE 1

Benzyl 2-(2,2-difluorocyclopropyl)acetate 80 g (454 mmol) Benzyl 3-butenoate was dissolved in 250 ml diethylene glycol dimethyl ether (diglyme) and reacted at 165° C. over 4 hours with a solution of 138 g (908 mmol) sodium chlorodifluoroacetate, dissolved in 250 ml diglyme. The mixture was then stirred for an hour at 165° C. and cooled. The precipitated sodium chloride was removed and washed with 100 ml diglyme. The filtrate was concentrated in vacuo (35° C., oil pump) and the residue taken up in 500 ml ether, the extract washed twice each time with 100 ml water and dried over magnesium sulphate. After evaporation, the residue was fractionated under an oil pump vacuum, on a spiny column and a sample analysed by thin layer chromatography (hexane:ethyl acetate=1:1) (Rf=0.64).

Yield: 82.4 g (80% of theory).
b.p.$_{0.05}$: 90° C.
$n_D^{20}$: 1.4783.

PREPARATION OF THE STARTING MATERIAL

Benzyl 3-butenoate 138 g (535 mmol) Triphenylphosphine and 84 ml (812 mmol) benzyl alcohol were added dropwise to 46 g (535 mmol) 3-butenoic acid dissolved in 500 ml ether and 87 ml (535 mmol) ethyl azodicarboxylate and the mixture stirred for 7 hours and allowed to stand overnight. After evaporation of the solvent, the residue was purified by column chromatography (silica gel, hexane/ethyl acetate=95:5) and a sample analysed by thin layer chromatography (hexane:ethyl acetate=1:1) (Rf=0.61).

Yield: 83.5 g (88% of theory).
$n_D^{20}$: 1.5084.

EXAMPLE 2

2,2-Difluorocyclopropylacetic acid 142.3 g (630 mmol) Benzyl 2-(2,2-difluorocyclopropyl)acetate was added dropwise to a solution of 35.2 g (630 mmol) potassium hydroxide in 360 ml methanol with ice-cooling and the mixture stirred for 3 hours at room temperature. It was then concentrated on a rotary evaporator, the precipitated potassium salt separated and washed three times with ether. The salt was dissolved in 150 ml water, the solution acidified with 54 ml concentrated sulphuric acid and extracted three times, each time with 200 ml ethyl acetate. The ethyl acetate phase was washed twice with water, dried over magnesium sulphate and concentrated at 40° C. at atmospheric pressure. It was then fractionated under vacuum (17 mbar) and analysed by thin layer chromatography (dichloromethane:methanol=95:5) (Rf=0.20).

Yield: 82 g (96% of theory).
b.p.$_{17}$: 99°-100° C.

EXAMPLE 3

Tetradecyl 2-(2,2-difluorocyclopropyl)acetate

A solution of 2.08 g (9.7 mmol) 1-tetradecanol in 20 ml tetrahydrofuran (THF) was treated with 200 mg 4-dimethylaminopyridine (DMAP) and 1.35 ml (9.7 mmol) triethylamine and cooled to 0° C. A solution of 1.5 g (9.7 mmol) 2-(2,2-difluorocyclopropyl)acetyl chloride in 10 ml tetrahydrofuran at 0°-5° C. was added dropwise. The mixture was then stirred for 2 hours at room temperature. The precipitated triethylamine hydrochloride was separated, the solution concentrated under reduced pressure, and the residue dissolved in 50 ml diethyl ether. After washing with in turn 10 ml water, 10% caustic soda and water until neutral, the ether solution was dried over magnesium sulphate and evaporated in vacuo (200 mbar). The residue was distilled under an oil pump vacuum.

Yield: 2.2 g (68% of theory).
b.p. (200 mbar): 110° C.

PREPARATION OF THE STARTING MATERIAL

2-(2,2-difluorocyclopropyl)acetyl chloride

A mixture of 39.8 g (0.29 mmol) 2,2-difluorocyclopropylacetic acid and 38.5 ml (0.53 mmol) thionyl chloride was heated under reflux for 5 hours. Excess thionyl chloride was distilled and the residue was distilled in vacuo.

Yield: 43 g (95% of theory).
b.p. (200 mbar): 94° C.

EXAMPLE 4

4'-Chloro-2-(2,2-difluorocyclopropyl)acetanilide 15.3 g (120 mmol) 4-Chloroaniline, 18.4 ml (132 mmol) triethylamine and 50 mg dimethylaminopyridine dissolved in 150 ml tetrahydrofuran was treated, under ice-cooling, with 18.6 g (120 mmol) 2-(2,2-difluorocyclopropyl)acetyl chloride. The mixture was stirred for 2 hours at room temperature and poured into 1000 ml water. The precipitated crystals were separated, washed with a small amount of hydrochloric acid and dried in vacuo (200 mbar). A sample was analysed by thin layer chromatography (dichloromethane:methanol=95:5) (Rf=0.62).

Yield: 25.8 g (87% of theory).
m.p. 111°-112° C.

EXAMPLE 5

4'-Chloro-N-[2-(2,2-difluorocyclopropyl)ethyl]aniline 4.9 g (20 mmol) 4'-Chloro-2-(2,2-difluorocyclopropyl)acetanilide was dissolved in 75 ml tetrahydrofuran (THF) and treated with 60 ml (60 mmol) of a one molar solution of borane in THF. After 7 hours, it was decomposed with aqueous potassium carbonate and extracted with diethyl ether. After evaporation in vacuo, it was dried under an oil pump vacuum (200 mbar) and purified by column chromatography (silica gel, hexane:ethyl acetate=95:5). A sample was analysed by thin layer chromatography (hexane:ethyl acetate=8:2) (Rf=0.40).

Yield: 4.6 g (100% of theory).
$n_D^{20}$: 1.5307.

EXAMPLE 6

4'-Chloro-N-[2-(2,2-difluorocyclopropyl)ethyl]-chloracetanilide 2.4 g (21 mmol) Chloroacetyl chloride, dissolved in 5 ml tetrahydrofuran, was added dropwise at 0° C. to a solution of 4.5 g (19 mmol) 4'-chloro-N-[2-(2,2-difluorocyclopropyl)ethyl]aniline, 2.9 ml (21 mmol) triethylamine and 400 mg dimethylaminopyridine in 100 ml tetrahydrofuran and the mixture stirred for 2 hours at room temperature. The precipitated crystals was separated and the solution concentrated in vacuo (ca. 200 mbar). The residue was purified by column chromotography (silica gel, hexane/ethyl acetate=95:5). A sample was analysed by thin layer chromatography (hexane:ethyl acetate=9:1) (Rf=0.14).

Yield: 4.1 g (70% of theory).
$n_D^{20}$: 1.5310.

EXAMPLE 7

2-(2,2-Difluorocyclopropyl)ethyl 3,4-dichlorophenylcarbamate 2 g (16 mmol) 2-(2,2-Difluorocyclopropyl)ethanol, dissolved in 5 ml tetrahydrofuran (THF) was treated with 3 g (16 mmol) of 3,4-dichlorophenyl isocyanate. After 6 hours reaction time at room temperature, the mixture was concentrated in vacuo and the residue recrystallised from cyclohexane. A sample was analysed by thin layer chromatography (hexane:ethyl acetate=1:1) (Rf=0.54).

Yield: 3.2 g (100% of theory).
m.p. 89°–90° C.

In a similar manner, the following compounds were prepared.

general formula $R^1, R^2, R^3, R^4 = H$

| Example No. | $R^5$ | $R^6$ | $n_D^{20}$ | m.p. | b.p. |
|---|---|---|---|---|---|
| 8 | 2-Cl-C6H4 | —C2H5 | 1.5067 | | |
| 9 | 3-Cl-C6H4 | —C2H5 | 1.5116 | | |
| 10 | 4-Cl-C6H4 | —C2H5 | 1.5134 | | |
| 38 | 3,4-Cl2-C6H3 | H | | 79–80 | |
| 39 | 2,3-(CH3)2-C6H3 | H | | 95–96 | |
| 47 | —(CH2)5— | | 1.4634 | | |
| 48 | —(CH2)2—O—(CH2)2— | | 1.4659 | | |
| 49 | 4-C12H25-C6H4 | H | 1.5029 | | |
| 50 | —C16H33 | H | | 68–69° C. | |
| 51 | —C18H37 | H | | 73–75° C. | |
| 52 | 1-naphthylmethyl | H | | 100–102° C. | |
| 53 | 4-(isopropyl)phenoxyphenyl | H | 1.5289 | | |

-continued general formula

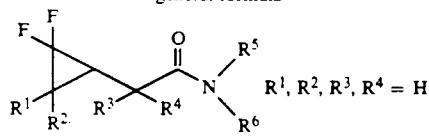

$R^1, R^2, R^3, R^4 = H$

| Example No. | R⁵ | R⁶ | Physical Constant |||
|---|---|---|---|---|---|
| | | | $n_D^{20}$ | m.p. | b.p. |
| 54 | [3-phenoxyphenyl with ethyl linker] | H | | | |
| 55 | [CH₃-C≡C-CH₂-] | H | | 56–57° C. | |
| 56 | [phenyl-OBzl with methylene] | H | | 157–158° C. | |
| 57 | [phenanthren-9-yl with methylene] | H | | 172–173° C. | |
| 58 | [naphthalen-2-yl with ethyl linker] | H | | | |
| 59 | $-C(CH_2-O-\overset{O}{\underset{\phantom{.}}{C}}\text{-CH}_2\text{-cyclopropyl}(F,F))_3$ | H | | | |
| 60 | [4-hydroxyphenyl methylene] | H | | | |
| 61 | [4-(propargyloxy)phenyl methylene] | H | | | |
| 62 | [4-(tosyloxy)phenyl methylene] | H | | | |
| 63 | [3-ethoxyphenyl-CH(CF₃)-] | H | | 85° C. | |
| 64 | [imidazol-1-yl methylene] | H | | | |

-continued
general formula
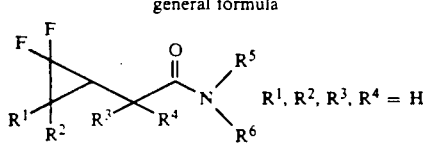
R¹, R², R³, R⁴ = H
| Example No. | R⁵ | R⁶ | Physical Constant |||
|---|---|---|---|---|---|
| | | | $n_D^{20}$ | m.p. | b.p. |
| 65 | cyclohexyl | cyclohexyl | | | |
| 66 | —H | H | | | |
| 67 | —C(O)—C₆H₅ (phenacyl) | H | | | |
| 68 | 1-methylindol-3-yl | 1-methylindol-3-yl | | | |
| 69 | —C₆H₄—C₄H₉ (p) | H | | 50° C. | |
| 70 | —CH₂C(CH₃)₂—C₆H₅ | H | | 84–85° C. | |
| 71 | 1-Adamantyl | H | | | |
| 72 | —C₅H₁₁ | —C₅H₁₁ | | | |
| 73 | —CH₂—C₆H₅ | H | | 58–59° C. | |
| 74 | —C₆H₄—OCH₂CF₃ (p) | H | | | |
| 75 | —C₆H₄—O—(benzothiazol-2-yl) (p) | H | | | |
| 76 | (2,2-difluorocyclopropyl)CH₂—C(O)O—C₆H₄—CH₃ (p) | H | | | |
| 90 | —CH₂CH₂NHC(=CHNO₂)— | | | 173.2° C. | |

-continued
general formula
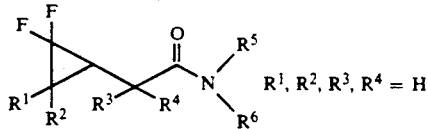  R¹, R², R³, R⁴ = H
| Example No. | R⁵ | R⁶ | Physical Constant $n_D^{20}$ | m.p. | b.p. |
|---|---|---|---|---|---|
| 108 | 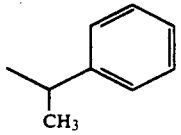 | | $R_F$ = 0.40 (Hex/EE = 1/1) | | |
| 109 | 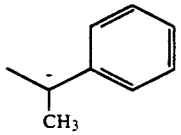 | | $R_F$ = 0.33 (Hex/EE = 1/1) | | |
Hex = Hexane
EE = Diethylethyl
general formula
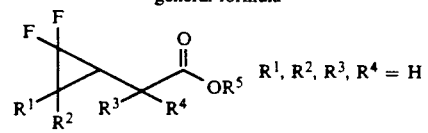  R¹, R², R³, R⁴ = H
| Example No. | R⁵ | Physical Constant $n_D^{20}$ | m.p. | b.p. |
|---|---|---|---|---|
| 11 | —C₁₆H₃₃  | | | 131/0.02 mbar |
| 12 | 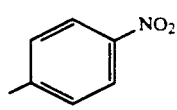 | 1.5198 | | 120/0.02 mbar |
| 13 |  | 1.4053 | | |
| 14 | 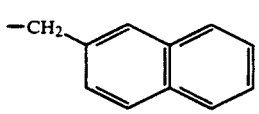 | | | 135/0.02 mbar |
| 15 | 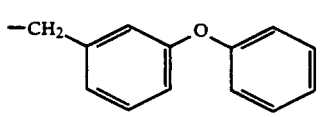 | 1.5331 | | |
| 16 | 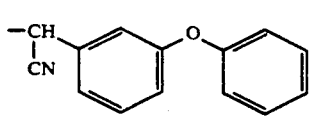 | 1.5457 | | |
| 17 | 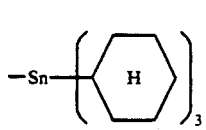 | | 93° C. | |

-continued
general formula
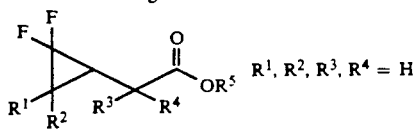
R¹, R², R³, R⁴ = H
| Example No. | R⁵ | Physical Constant | | |
|---|---|---|---|---|
| | | n_D^{20} | m.p. | b.p. |
| 18 | —CH₂—(pentafluorophenyl) | 1.4350 | | |
| 77 | —(biphenyl) | | 73.6° C. | |
| 78 | —(C₆H₄)—CH₂—(C₆H₅) | 1.5331 | | |
| 79 | —CH₂CH=CH—(C₆H₅) | 1.5125 | | |
| 80 | —(methylindanyl) | 1.5017 | | |
| 81 | —(o-tert-butylphenyl)—C(CH₃)₃ | 1.4866 | | |
| 82 | —(menthyl-type group) | 1.4488 | | |
| 83 | —(decalinyl)—OOCCH₂CHCH₂ with CF₂ cyclopropane | 1.4597 | | |
| 84 | —(CH₂)₁₀—OOCCH₂CH—CH₂ with CF₂ | | 34° C. | |
| 85 | —CH₂C(CH₃)₂O—(C₆H₄)—Cl | 1.4890 | | |

-continued general formula

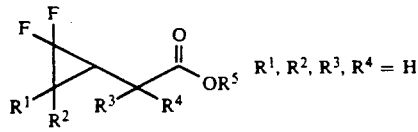

$R^1, R^2, R^3, R^4 = H$

| Example No. | R⁵ | $n_D^{20}$ | m.p. | b.p. |
|---|---|---|---|---|
| 86 | —CH(cyclopropyl)(4-Cl-C₆H₄) | 1.5028 | | |
| 87 | —CH₂C(CH₃)₂CH₂—(4-OCH₂CH₃-C₆H₄) | 1.4847 | | |
| 88 | methyldecahydronaphthyl | 1.4647 | | |
| 89 | —CH₂CH₂—C(=C(CH₃)-thiazolyl) | 1.4858 | | |
| 91 | menthyl (2-isopropyl-5-methyl-cyclohexyl with CH₃) | 1.4413 | | |
| 92 | Adamantanylmethyl | 1.4776 | | |
| 93 | —C(CH₃)₂—(2-naphthyl) | 1.5389 | | |
| 94 | —CH₂CH=C(CH₃)CH₂CH₂CH=C(CH₃)₂ | 1.4549 | | |
| 95 | —CH₂CH=C(CH₃)CH₂CH₂CH=C(CH₃)CH₂CH₂CH=C(CH₃)₂ | 1.4686 | | |
| 96 | —(CH₂)₆Cl | 1.4390 | | |
| 97 | —C₆H₄—CH₂COOCH₃ | 1.4873 | | |
| 98 | —(CH₂)₂—C≡C—(CH₂)₄CH₃ | 1.4396 | | |
| 99 | —CH₂CH₂OCH₂CH₂OOC—CH₂CH(CF₂)CH₂ | 1.4264 | | |
| 100 | —CH(CH₃)—C₆H₅ (Diastereomer mixture) | | | |

-continued
general formula
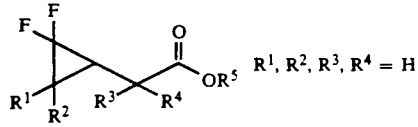  $R^1, R^2, R^3, R^4 = H$
| Example No. | $R^5$ | Physical Constant |||
|---|---|---|---|---|
| | | $n_D^{20}$ | m.p. | b.p. |
| 101 | 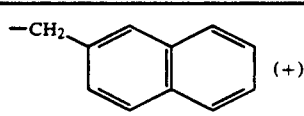 (+) | | | |
| 102 | 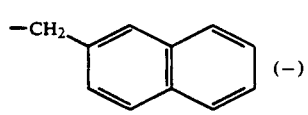 (−) | | | |
| 103 | 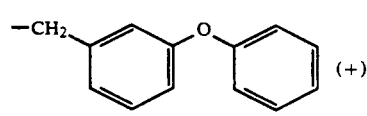 (+) | | | |
| 104 | 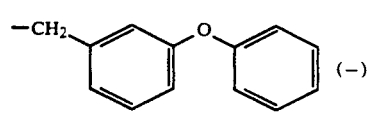 (−) | | | |
| 105 | 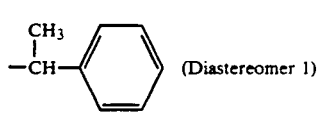 (Diastereomer 1) | | | |
| 106 | 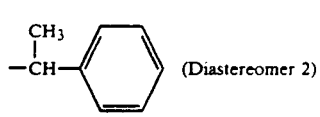 (Diastereomer 2) | | | |
| 107 | —CH(CH$_2$CH$_2$CH$_2$CH$_2$CH$_3$)$_2$ | 1.4249 | | |
| 110 | H (+) | | | |
| 111 | H (−) | | | |
general formula 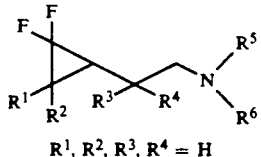
$R^1, R^2, R^3, R^4 = H$
| Example No. | $R^5$ | $R^6$ | Physical Constant |||
|---|---|---|---|---|---|
| | | | $n_D^{20}$ | m.p. | b.p. |
| 19 | 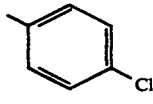 | 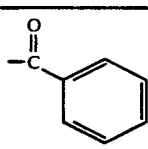 | 1.5628 | | |
| 20 | 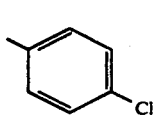 | 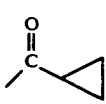 | 1.5236 | | |

-continued
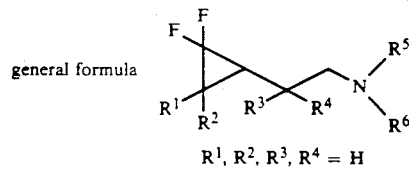
general formula
$R^1, R^2, R^3, R^4 = H$
| Example No. | $R^5$ | $R^6$ | $n_D^{20}$ | m.p. | b.p. |
|---|---|---|---|---|---|
| 21 | 3,4-diCl-phenyl | -CO-cyclopropyl | 1.5378 | | |
| 22 | 2,3-diCl-phenyl | -CO-phenyl | 1.5676 | | |
| 23 | 3,4-diCl-phenyl | -COCH$_2$Cl | 1.5437 | | |
| 24 | 4-Cl-phenyl | —CONHCH$_3$ | | 92-93° C. | |
| 25 | 4-Cl-phenyl | —COOCH$_3$ | 1.5075 | | |
| 26 | 4-Cl-phenyl | —COOCH(CH$_3$)$_2$ | 1.4944 | | |
| 27 | 3,4-diCl-phenyl | —CONHCH$_3$ | 1.5236 | 72-73° C. | |
| 28 | 3,4-diCl-phenyl | —COOCH$_3$ | 1.5220 | | |
| 29 | 3,4-diCl-phenyl | —COOCH(CH$_3$)$_2$ | 1.5063 | | |
| 30 | 3,4-diCl-phenyl | —COOCH$_2$CH$_2$CH$_2$CH$_3$ | 1.5080 | | |
| 31 | 2,6-diCH$_3$-phenyl | —COCH$_2$Cl | 1.5337 | | |

-continued
general formula 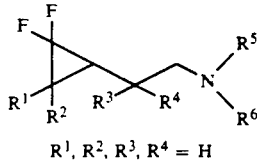
$R^1, R^2, R^3, R^4 = H$
| Example No. | $R^5$ | $R^6$ | $n_D^{20}$ | m.p. | b.p. |
|---|---|---|---|---|---|
| 32 | 2,3-(CH$_3$)$_2$-C$_6$H$_3$ | —CO-cyclopropyl | 1.5278 | | |
| 33 | 2,3-(CH$_3$)$_2$-C$_6$H$_3$ | —COOCH$_3$ | 1.5120 | | |
| 34 | 2,3-(CH$_3$)$_2$-C$_6$H$_3$ | —COOCH$_2$CH$_2$CH$_2$CH$_3$ | 1.5965 | | |
| 35 | 2,3-(CH$_3$)$_2$-C$_6$H$_3$ | —COOCH$_2$CH(CH$_3$)$_2$ | 1.4963 | | |
| 36 | 2,3-(CH$_3$)$_2$-C$_6$H$_3$ | —CO-O-C$_6$H$_5$ | 1.5470 | | |
| 37 | 2,3-(CH$_3$)$_2$-C$_6$H$_3$ | —CONHCH$_3$ | | 80–81° C. | |
| 40 | 3,4-Cl$_2$-C$_6$H$_3$ | H | 1.5439 | | |
| 41 | 2,3-(CH$_3$)$_2$-C$_6$H$_3$ | H | 1.5014 | | |
| 42 | [4-(2-methyl-benzodioxol-type) see structure] | H | 1.5110 | | | general formula 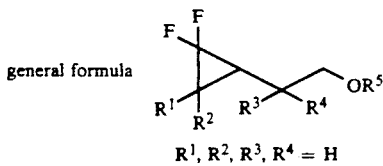

$R^1, R^2, R^3, R^4 = H$

| Example No. | $R^5$ | Physical Constant $n_D^{20}$ | m.p. | b.p. |
|---|---|---|---|---|
| 43 | 3-Cl-C6H4-NHCO- | | 54–55° C. | |
| 44 | 4-Cl-C6H4-NHCO- | | 64–65° C. | |
| 45 | 3-CF3-pyridin-2-yl-methylidene | 1.4376 | | |
| 46 | 3-Cl-5-CF3-pyridin-2-yl-methylidene | 1.4546 | | | general formula 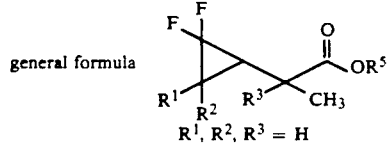

$R^1, R^2, R^3 = H$

| Example No. | $R^5$ | Physical Constant $n_D^{20}$ | m.p. | b.p. |
|---|---|---|---|---|
| 112 | —CH2—C6H5 (Diastereomer mixture) | 1.4726 | | |
| 113 | —C16H33 (Diastereomer mixture) | | | |
| 114 | 6-ethyl-naphthalen-2-yl (Diastereomer 1) | | | |
| 115 | 6-ethyl-naphthalen-2-yl (Diastereomer 2) | | | |

-continued general formula 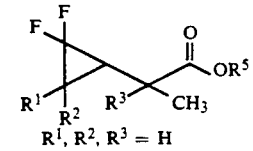

$R^1, R^2, R^3 = H$

| Example No. | $R^5$ | Physical Constant $n_D^{20}$ | m.p. | b.p. |
|---|---|---|---|---|
| 116 | 3-(phenoxy)-ethylphenyl (Diastereomer 1) | | | |
| 117 | 3-(phenoxy)-ethylphenyl (Diastereomer 2) | | | |
| 118 | methyl-biphenyl (Diastereomer 1) | | | |
| 119 | methyl-biphenyl (Diastereomer 2) | | | |

USE EXAMPLE A

Activity in the curative leaf treatment of field beans (Phaseolus vulgaris nanus Aschers.) against motile stages of the two spotted mite (Tetranychus urticae Koch)

Seedlings of field beans were grown in a warm glasshouse until full development of the primary leaf and then covered with pieces of leaf infested with Tetranychus urticae. One day later, the leaf pieces were removed and the plants were sprayed until dripping wet with an aqueous preparation containing 0.1% active ingredient. After 7 days at 22°–24° C., the number of dead motile stages of Tetranychus on the treated and untreated plants was determined. From this the activity of the treatment was calculated using Abbott's method.

The compounds of the invention of Examples 1–5, 7–18, 20–22, 24, 25, 27, 28, 34, 38, 40, 43, 44 and 46 had an activity of 80–100%.

USE EXAMPLE B

Activity in the curative leaf treatment of field beans (Phaseolus vulgaris nanus Aschers.) against eggs of the two spotted mite (Tetranychus urticae Koch)

Seedlings of field beans were grown in a warm glasshouse until full development of the primary leaf and then treated adult female Tetranychus urticae. One day later, the plants, on which eggs had been laid, were sprayed until dripping wet with an aqueous preparation containing 0.1% active ingredient. After 7 days at 22°-24° C., the number of dead eggs on the treated and untreated plants was determined. From this the activity of the treatment was calculated using Abbott's method.

The compounds of the invention of Examples 1-4, 7-22, 24, 25, 27, 28, 34, 38, 40-44 and 46 had an activity of 80-100%.

USE EXAMPLE C

Activity in prophylactic treatment of leaves against brown rice-hoppers (*Niliparvata lugens* Stal)

Rice seedlings (about 15 per pot) were grown in a warm glasshouse, until formation of the third leaf and then sprayed, until dripping wet, with an aqueous preparation containing 0.1% of active material. After drying the sprayed leaves, a transparent cylinder was placed over each pot. 30 Adult brown rice-hoppers (*Niliparvata lugens*) were introduced into each pot. After 2 days at 26° C. in the glasshouse, the amount of dead hoppers was determined. The activity was calculated using to Abbott's method in comparison with a few untreated remaining control pots.

The compounds of the invention of Examples 4, 5, 9, 17, 21, 26, 28, 29, 32, 34-36, 40 and 41 had an activity of 80-100%.

USE EXAMPLE D

Activity in the curative treatment of broad beans (*Vicia fabae* L.) against black bean aphids (*Aphis fabae* scop.)

Seedlings of broad beans (*Vicia fabae*), one plant per pot, were grown in a warm glasshouse, to a height of about 6 cm. The plants were then covered with a culture of black bean aphid (*Aphis fabae*). After each plant had been colonised with 100 to 200 insects, they were each sprayed with an aqueous preparation of each respective active ingredient at a concentration of 0.1%, until dripping wet, and left in the glasshouse at about 24° C. After 2 days the amount of dead aphids was ascertained. The activity was calculated using to Abbott's method in comparison with a untreated remaining control pots.

The compounds of the invention of Examples 1, 4 and 18 had an activity of 80-100%.

USE EXAMPLE E

Activity against larvae of the diamond-backed moth (*Plutella xylostella*)

The compounds of the invention were made up as aqueous emulsions at a concentration of 0.1%. Kohlrabi leaves (*Brassica olearacea* var. gongylodes), placed in polystyrene petri dishes, were sprayed with these preparations (4 mg spray/cm$^2$). After the sprayed surface had dried, 10 young larvae of the diamond-backed moth (*Plutella xylostella*) were placed in each petri dish and exposed to the treated food in the closed dishes for two days. The % mortality of the larvae after two days indicated the level of activity.

Compounds of Examples 17 and 28 showed 80-100% activity.

USE EXAMPLE F

Activity against eggs/larvae of the corn rootworm (*Diabrotica undecimpunctata*)

The compounds of the invention were made up as aqueous emulsions at a concentration of 0.1%. The soil in polystyrene petri dishes, containing maize seedlings (1 seedlings/dish) and ca. 50 eggs of the corn rootworm (*Diabrotica undecimpunctata*) were sprayed with these preparations (4 mg spray/cm$^2$). The closed dishes were left at 25° C. under extended daylight conditions for 4 days. The criterion for judging the activity was the death of eggs or newly hatched larvae at thec end of the test.

Compounds of Examples 35, 40 and 45 showed 100% activity.

USE EXAMPLE G

Activity against gravid female ticks (*Boophilus microplus*—Paquera strain)

Groups of 5 mature female cattle ticks were dipped for 10 minutes in aqueous-acetone solvent dispersions of test compound containing a wetting agent, dried and then placed in individually compartmented plastic containers held at 25° C. and >80% R. H., until mortality of ticks or fecundity and viability of eggs produced by survivors could be assessed. The percentage reduction in total reproductive capacity (i.e. the combined effects of adult mortality, reduced fecundity and mortality of eggs) was then recorded and compared with controls. The controls gave less than 5% reduction of reproductive capacity whereas compounds of Examples 1, 3, 14, 15, 16 and 18 gave at least 50% reductions of reproductive capacity at a concentration of 500 mg/liter or less.

We claim:

1. Compound of formula II

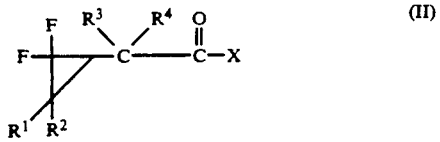

in which $R^{1-4}$ are hydrogen, and X is Cl or Br.

2. Compound according to claim 1 in which X is Cl.
3. Compound according to claim 1 in which X is Br.
4. Compound of the formula

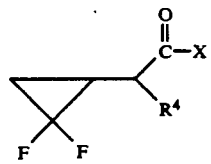

in which $R^4$ is $C_{1-6}$-alkyl or halogen and X is OH, Cl or Br.

5. Compound of claim 4 in which $R^4$ is methyl.

* * * * *